United States Patent [19]

Rovnyak

[11] 4,002,749
[45] Jan. 11, 1977

[54] SUBSTITUTED INDOLINONES
[75] Inventor: George C. Rovnyak, Hopewell, N.J.
[73] Assignee: E. R. Squibb & Sons, Inc., Princeton, N.J.
[22] Filed: Aug. 12, 1975
[21] Appl. No.: 604,000
[52] U.S. Cl. .............................. 424/246; 424/270; 260/240 F; 260/240.7; 260/243 R; 260/306.7 T
[51] Int. Cl.² ....................................... C07D 417/02
[58] Field of Search ........ 260/243 R, 240 F, 240.7, 260/306.8 R; 424/246, 270

[56] References Cited
UNITED STATES PATENTS
3,853,857  10/1974  Narayanan et al. ........... 260/240 G OTHER PUBLICATIONS
Bergmann et al., Chem. Abstracts, vol. 69, Abst. No. 86,750d (1968).
Tacconi et al., Chem. Abstracts, vol. 75, Abst. No. 63,654k (1971).

Primary Examiner—John D. Randolph
Attorney, Agent, or Firm—Lawrence S. Levinson; Merle J. Smith; Burton Rodney

[57] ABSTRACT

Indolinone compounds which exhibit anti-inflammatory activity have the following formula

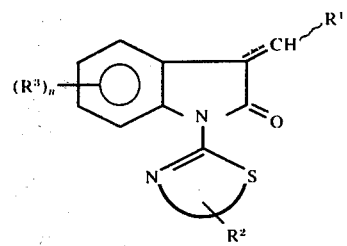

wherein $R^1$, $R^2$, $R^3$,

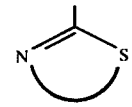

and $n$ are as defined herein.

25 Claims, No Drawings

SUBSTITUTED INDOLINONES

The present invention relates to thiazolinyl and thiazinyl derivatives of indolinones having the structure

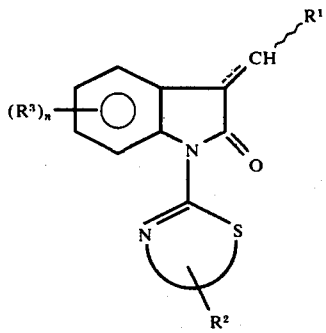
I wherein
- R¹ is aryl, substituted aryl, or heteroaryl;
- R² is hydrogen, lower alkyl, aryl or lower alkylaryl;
- R³ is hydrogen, lower alkyl, trifluoromethyl, halo, amino, lower alkoxy, nitro, cyano, acyl, aroyl, or dilower alkylamino;
- n is 1 or 2; and the dotted line used in conjunction with the solid line ($=\!\!=$) represents a single or double bond; in the case where $=\!\!=$ is a single bond the carbon linked to R¹ will include two hydrogen substituents.

The radical

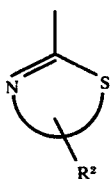

represents a 5- or 6-membered ring containing three or four carbons, respectively, wherein the additional two or three carbons (not shown) may include a substituent other than hydrogen as indicated above.

The lower alkyl groups represented by the above R groups include straight or branched chain aliphatic hydrocarbon radicals having up to seven carbon atoms, such as methyl, ethyl, propyl, isopropyl, butyl, isobutyl, t-butyl, amyl, hexyl, heptyl, and the like.

The lower alkoxy group can be represented by the formula lower alkyl-O- and this includes straight and branched chain radicals of up to and including seven carbon atoms, corresponding to the above alkyl groups, e.g., methoxy, ethoxy, propoxy, isopropoxy, and the like.

The term halogen includes each of the four halogens, but fluorine and chlorine are preferred.

Examples of the di-lower alkyl amino group wherein lower alkyl is defined herein include dimethylamino, diethylamino, ethylmethylamino, butylmethylamino, ethyl i-propylamino and the like.

The term "aryl" includes monocyclic or bicyclic monovalent aromatic ring systems such as phenyl or naphthyl.

The term "substituted aryl" includes aryl groups as defined above which include one or more substituents such as halogen, hydroxy, lower alkyl, nitro, trifluoromethyl, and lower alkoxy.

The acyl and aroyl groups included herein are derived from hydrocarbon carboxylic acids of less than twelve carbon atoms, which may be exemplified by the lower alkanoic acids (e.g., formic, acetic, propionic, butyric, valeric, trimethyl acetic and caproic acids), the lower alkenoic acids (e.g., acrylic, methacrylic, crotonic, 3-butenoic and senecioic acids), the monocyclic arylcarboxylic acids (e.g., benzoic and toluic acids), the monocyclic aryl-lower alkanoic acids [e.g., phenacetic, β-phenylpropionic, α-phenylbutyric, and 5-(p-methylphenyl) pentanoic acids], the cycloalkyl carboxylic acids (e.g., cyclobutane carboxylic acid, cyclopentane carboxylic acid and cyclohexane carboxylic acid), the cycloalkenyl carboxylic acids (e.g., 2-cyclobutene carboxylic acid and 3-cyclopentene carboxylic acid), the cycloalkyl and cycloalkenyl-lower alkanoic acids [e.g., cyclohexaneacetic, α-cyclopentanebutyric, 2-cyclopenteneacetic and 3-(3-cyclohexene)pentenoic acid], and the like. Thus, the above acyl and aroyl groups may be represented by the formula

wherein R may be lower alkyl, lower alkenyl, aryl, aryl-lower alkyl, cycloalkyl, cycloalkenyl, cycloalkyl-lower alkyl, and cycloalkyl-lower alkenyl.

The term "heteroaryl" as employed herein includes heterocyclic groups such as thienyl, furyl, chlorofuryl, dichlorofuryl, pyrryl, pyridyl, coumarinyl, thiacoumarinyl, thiazolyl, isothiazolyl or imidazolyl.

Thus, compounds of formula I can have the following structures:

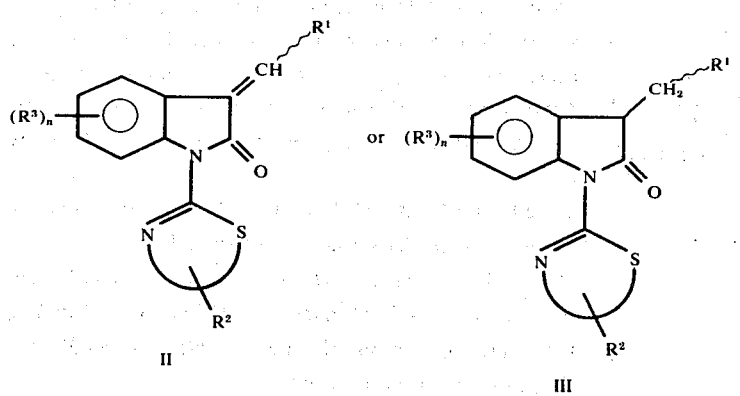

Preferred are those compounds of formula II and III wherein $R^3$ is hydrogen, $R^2$ is hydrogen,

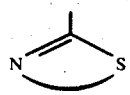

is a 5- or 6-membered ring, and $R^1$ is phenyl.

The compounds of the present invention can be prepared as follows.

Compounds of formula IV are prepared by reacting compounds of formula V with a haloalkyl isothiocyanate of formula VI in a molar ratio of from 2:1 to 1:10, in the presence of a base such as sodium hydride, in a non-polar aprotic solvent such as glyme, toluene or tetrahydrofuran, at or near the reflux temperature for from 1 to 24 hours, in accordance with the following reaction

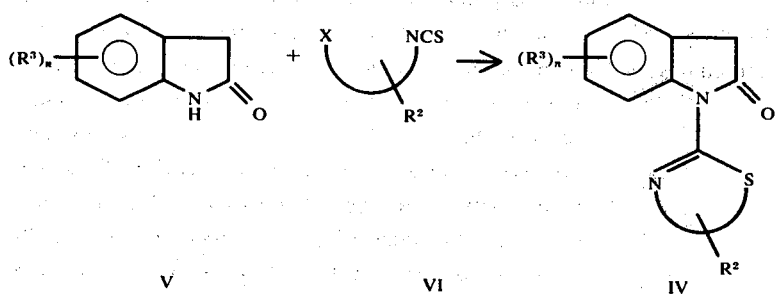

wherein X is Cl or Br and the portion

(which links N and X) in structure VI represents a chain of two or three carbons, one carbon of which may include the $R^2$ substituent other than hydrogen.

Compounds of formula II can then be prepared by treating compounds of formula IV with an aldehyde of formula VII in a molar ratio of from 1:1 to 1:2 in the presence of a base, such as piperidine, in a non-polar aprotic solvent such as benzene, at or near the reflux temperature for from 0.5 to 24 hours, in accordance with the following reaction

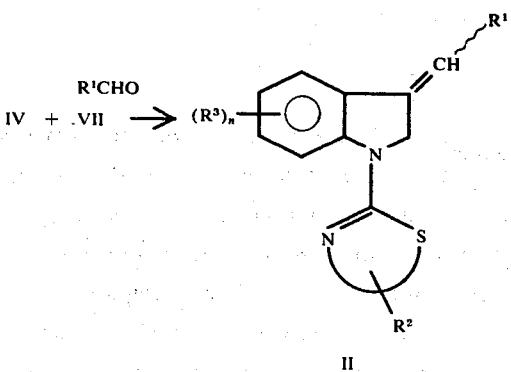

The stereochemistry of $R^1$ is determined by the nature of this group. Thus, for example, when $R^1$ is phenyl or 3- and/or 4-substituted phenyl the function $R^1$ is trans to the carbonyl. When $R^1$ is 2-OH phenyl, 2-thienyl or 2-pyridyl the function $R^1$ is primarily or exclusively cis to the carbonyl.

Alternatively, compounds of formula II can be prepared by first reacting compounds of formula V with an aldehyde of formula VII under the conditions employed above to form a compound of formula VIII and further reacting the compound of formula VIII with a haloalkylisothiocyanate of formula VI under the conditions employed above, in accordance with the following reactions.

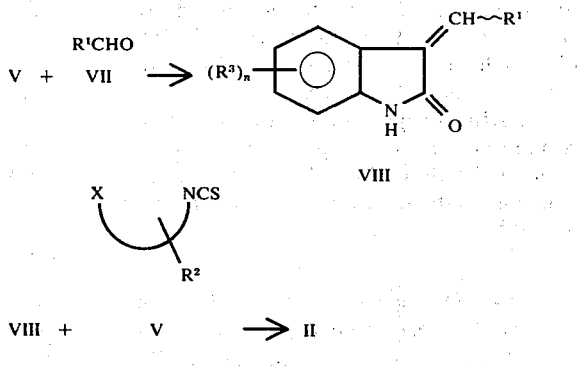

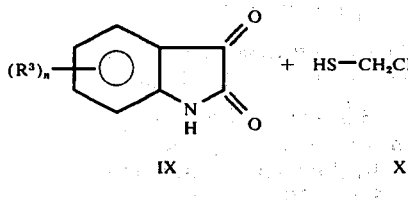

The stereochemistry of $R^1$ of II, thus obtained, is the same as set out above.

Compounds of formula IV, used as intermediates in the preparation of compounds of formula II, can also be prepared by first reacting compounds of formula IX with an $\alpha,\omega$-alkane dithiol of formula X such as 1,2-ethanedithiol, using conditions described in the literature [HOAC, $BF_3OEt_2$; J.A.C.S., 80, 5575 (1958)] to give compounds of formula XI.

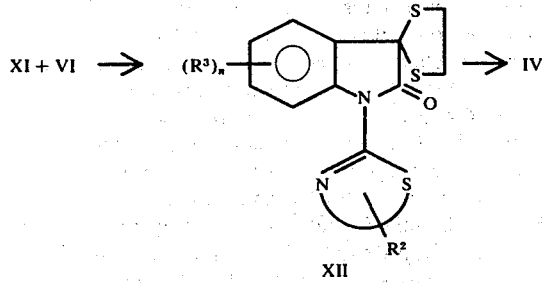

Compounds of formula XI can then be reacted with a haloalkylisothiocyanate of formula VI under the conditions as described above to give compounds of formula XII which, in turn, can be reacted with Raney nickel in non-polar aprotic solvents, such as toluene, at or near the reflux temperature for from 0.5 to 24 hours to give compounds of formula IV.

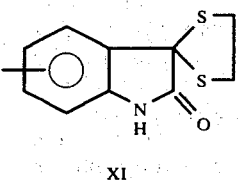

Compounds of formula III can be prepared by reacting compounds of formula II with hydrogen in the presence of a catalyst such as Raney nickel in a polar solvent such as ethanol, at a pressure of from 3–5 atmospheres, at or near ambient temperature, for from 0.5 to 8 hours.

Compounds of the invention of formula I wherein $R_3$ is amino can be prepared from the corresponding compounds wherein $R^3$ is nitro by reducing the nitro group in accordance with conventional techniques.

A variety of nuclear substituted oxindole derivatives are available. General methods of syntheses are reviewed in several texts:
1. The Chemistry of Heterocyclic Compounds A. Weissberger, ed. Vol. 8 Interscience Publishers, Inc. N.Y. (1954)
2. Heterocyclic Compounds R. C. Elderfield Vol. 3, John Wiley & Sons, Inc. N.Y. (1952)
3. The Chemistry of Indoles, R. J. Sundberg Academic Press, N.Y. (1970)

In addition, articles by P. G. Gassman outline another general method of synthesis of oxindoles.
1. J.A.C.S. 96 5508 (1974)
2. J.A.C.S. 96 5512 (1974)

The compounds of formula I form physiologically acceptable acid-addition salts with inorganic and organic acids. These acid-addition salts frequently provide useful means for isolating the products from reaction mixtures by forming the salt in a medium in which it is insoluble. The free base may then be obtained by neutralization, e.g., with a base such as sodium hydroxide. Then any other salt may again be formed from the free base and the appropriate acid. Illustrative are the hydrohalides, especially the hydrochloride and hydrobromide which are preferred, sulfate, nitrate, phosphate, oxalate, tartrate, maleate, fumerate, citrate, succinate, methanesulfonate, benzenesulfonate, toluenesulfonate, and the like.

The compounds of the invention are useful as antiinflammatory agents and are effective in the prevention and inhibition of granuloma tissue formation in warm blooded animals, and may be used, for example, in a manner similar to phenylbutazone or indomethacin.

They may be used to decrease joint swelling, tenderness, pain and stiffness in mammalian species, such as dogs and monkeys, e.g., in conditions such as rheumatoid arthritis. Compounds of formula I or a physiologically acceptable acid-addition salt thereof may be compounded for such use according to accepted pharmaceutical practice in oral dosage forms such as tablets, capsules, elixirs or powders for administration of about 100 mg to 2 gm per day, preferably 100 mg to 1 gm per day in two to four divided doses.

The following examples further illustrate and represent preferred embodiments of the invention. All temperatures are expressed in degrees Centigrade.

EXAMPLE 1

1-(4,5-Dihydro-2-thiazolyl)-1,3-dihydro-3-(phenylmethylene)-2H-indol-2-one

A. 3-Benzylidene indolin-2-one

A solution of oxindole (49.5 g, 0.37 mole), benzaldehyde (50 ml, 0.5 mole) and piperidine (2 ml) in 500 ml of benzene is heated at reflux temperature, with removal of water, for one hour. Benzene is removed in vacuo and the residue is crystallized from ethanol to give 69.6 g of 3-benzylidene indolin-2-one (m.p. 177°–179°).

B. 1-(4,5-Dihydro-2-thiazolyl)-1,3-dihydro-3-(phenylmethylene)-2H-indol-2-one To a slurry of NaH (530 mg, 22 mM) in tetrahydrofuran (50 ml) at room temperature under $N_2$ is added a solution of 3-benzylidene indolin-2-one prepared as described in part A (4.42 g, 20 mM) in tetrahydrofuran (150 ml). After the addition is complete, the solution is stirred for 1 hour. To this solution is added a solution of 2-chloroethylisocyanate in tetrahydrofuran (50 ml) at room temperature. The reaction mixture is stirred at room temperature for 1 hour, then heated at reflux temperature for 3 hours. Solvent is removed in vacuo and the residue is dissolved in $CHCl_3$ and washed with 10% HCl and $H_2O$ (2X), dried ($CaCl_2$), treated with Darco and concentrated in vacuo to give 6.5 g of an oil. The product is obtained by column chromatography on alumina (neutral, Act I, 200 g) and elution with ethyl acetate/cyclohexane (0/100 to 20/80). The product, thus obtained (2.42 g), is twice crystallized from acetone/hexane to give 1.6 g of the title compound (26%), m.p. 120°–125°.

EXAMPLE 2

1-(5,6-Dihydro-4H-1,3-thiazin-2-yl)-1,3-dihydro-3-(phenylmethylene)-2H-indol-2-one To a slurry of NaH (1.44 g, 0.06 mole) in dry tetrahydrofuran (150 ml) at room temperature is added 3-benzylidene indolin-2-one (11.05 g, 0.05 mole, prepared as described in Example 1A) in tetrahydrofuran (150 ml). The solution is stirred at room temperature for 2 hours.

To the above solution at room temperature is added a solution of 3-bromopropylisothiocyanate in tetrahydrofuran (150 ml). The reaction mixture is then heated at reflux temperature overnight.

Tetrahydrofuran is removed in vacuo and the residue is partitioned between $CHCl_3$ and 10% aqueous HCl. The organic fraction is washed with $H_2O$ (3X), dried ($CaCl_2$), treated with Darco and concentrated in vacuo to give 16.8 g. of a dark viscous oil. The oil is extracted with boiling cyclohexane, containing a small amount of acetone, several times. The combined extracts, upon cooling, give 5.4 g of a solid. Recrystallization from acetone-hexane gives 4.3 g of the title compound, (27%): m.p. 123°–125°.

EXAMPLE 3

1-(4,5-Dihydro-2-thiazolyl)-1,3-dihydro-3-[(4-methoxyphenyl)methylene]-2H-indol-2-one

A. 1-(2-Thiazolin-2-yl)-indolin-2-one

To a solution of 4.0 g (0.03 mole) of oxindole in 125 ml dry glyme there is added 1.4 g (0.03 mole) of sodium hydride (50% oil dispersion) and the mixture is stirred at room temperature for 3 hours. Then 3.6 g (0.3 mole) of 2-chloroethyl isothiocyanate in 5 ml of dry glyme is added and the mixture is refluxed overnight. After evaporation of the solvent in vacuo, the residue is chromatographed on an Alumina Act. IV column. Elution with ethyl ether yields the product which is crystallied from ethyl ether to yield 0.6 g, m.p. 97°–99°.

B. 1-(4,5-Dihydro-2-thiazolyl)-1,3-dihydro-3-[(4-methoxyphenyl)methylene]-2H-indol-2-one To a warmed benzene solution of 1-(2-thiazolin-2-yl)-indolin-2-one (2.0 g, 7.2 mmol) and p-methoxybenzaldehyde (1.5 g, 11 mmole) is added piperidine (0.6 ml). The mixture is heated at reflux temperature for 2 hours. The reaction mixture is then washed with $NaHSO_3$ solution, diluted HCl and water. The organic phase is dried over anhydous $MgSO_4$ and concentrated in vacuo. The residue is recrystallized once each from acetone/hexane, acetonitrile and $CHCl_3$/methanol and gives 1.3 g (43%) of the product (m.p. 164.5°–167° C, softens at 149° C).

EXAMPLE 4

3-[(4-Chlorophenyl)methylene]-1-(4,5-dihydro-2-thiazolyl)-1,3-dihydro-2H-indol-2-one To a slurry of NaH (530 mg, 22 mmole) in dry tetrahydrofuran (50 ml) at room temperature is added a solution of 3-(4-chlorobenzylidene)-indolin-2-one, (m.p. 191°–193°, 5.2 g, 20.4 mmole, prepared from 2-oxindole and p-chlorobenzaldehyde by the method as described in Example 1) in tetrahydrofuran (100 ml). Additional NaH (100 mg) is added portionwise until no further gas evolution is noted. The solution is then stirred for 0.5 hour at room temperature.

To the above solution is added a solution of 2-chloroethyl isothiocyanate (2.21 g, 21 mmole) in tetrahydrofuran (75 ml). The mixture is stirred at room temperature for 0.5 hour, then heated at reflux temperature for 3 hours.

Tetrahydrofuran is removed in vacuo and the residue is partitioned between $CHCl_3$ and $H_2O$. The organic layer is washed with 10% HCl and $H_2O$ (2 X), dried ($CaCl_2$), treated with Darco and concentrated in vacuo to give 6.4 g of semi-solid. A portion (1.5 g) of the product is obtained by crystallization from acetone-hexane. The remainder, after evaporation of solvent in vacuo, is applied to a column (Neutral Alumina, Act I, 150 g, wet packed) and eluted with cyclohexane/ethyl acetate. The product (1.6 g) is eluted with 95/5 to 80/20 cyclohexane/ethyl acetate. This, combined with the 1.5 g portion above, is twice crytallized from ethanol to give 1.9 g of the product (30%); m.p. 153°–156° (softens 143°).

EXAMPLE 5

3-[3,4-Dichlorophenyl)methylene]-1-(4,5-dihydro-2-thiazolyl)-1,3-dihydro-2H-indol-2-one To a warmed mixture of 1-(2-thiazolin-2-yl)-indolin-2-one (prepared as described in Example 3A; 3 g, 13.8 mmole) and 3,4-dichlorobenzaldehyde (3.4 g, 19.3 mmole) in benzene (150 ml) is added a small amount of piperidine (about 1 ml). The solution is heated at reflux temperature for 2 hours, and then cooled to room temperature overnight. The reaction mixture is washed with $NaHSO_3$ solution, dilute HCl and water. The organic phase is dried over $CaCl_2$, treated with charcoal and concentrated in vacuo to give 3 g of a crude product. This is recrystallized twice from acetonitrile to give 1.0 g (20%) of the product: m.p. 182.5°–185° C.

EXAMPLE 6

1-(4,5-Dihydro-2-thiazolyl)-1,3-dihydro-3-[(2-hydroxyphenyl)methylene]-2H-indol-2-one To a warmed solution of 1-(2-thiazolin-2-yl)-indolin-2-one (prepared as described in Example 3A; 2.0 g; 9.2 mmole) and salicylaldehyde (1.6 g; 12.9 mmole) in dry benzene (100 ml) is added a small amount of piperidine (0.6 ml). The resultant mixture is heated at reflux temperature for 2 hours. The reaction mixture is extracted with dilute HCl solution (5 ml of concentrated HCl in 120 ml of water) twice. The acidic layers are combined and treated with saturated $NaHCO_3$ solution until pH paper indicates it is slightly basic. The precipitate is collected by filtration and washed well with water. This crude material is recrystallized from acetone/hexane (treated with charcoal) to give 1.9 g of the product: m.p. 195.5°–197° C.

EXAMPLE 7

1-(4,5-Dihydro-2-thiazolyl)-1,3-dihydro-3-(2-thienylmethylene)-2H-indol-2-one

A. 3-(2-Thienylmethylene)-indolin-2-one

A mixture of oxindole (16.5 g, 0.12 mole), thiophene-2-carboxaldehyde (19.1 g, 0.17 mole) and piperidine (1 ml) in 200 ml of benzene is heated at reflux temperature for 4 hours, during which time water is separated by means of a Dean-Stark trap. Solvent is removed in vacuo and the residue is crystallized twice from ethanol to give 15 g of the product: m.p. 208.5°–210°.

B.
1-(4,5-Dihydro-2-thiazolyl)-1,3-dihydro-3-(2-thienylmethylene)-2H-indol-2-one To a stirred suspension of NaH (0.51 gm; 21.1 mmole) in dry tetrahydrofuran (100 ml) is added dropwise a solution of 3-(2-thienylmethylene)-indolin-2-one prepared as described above (4.0 gm; 17.6 mmole) in dry tetrahydrofuran (100 ml). The resultant solution is stirred at room temperature for another hour, after which, it is cooled to 0° C in an ice bath, and a solution of chloroethylisothiocyanate (2.2 gm; 17.6 mmole) in dry tetrahydrofuran (50 ml) is added. The mixture is then heated at reflux temperature for 3.5 hours.

Tetrahydrofuran is removed in vacuo, the residue is brought into $CHCl_3$ (300 ml) and washed with dilute HCl (1X) and water (2X). The organic layer, after drying over anhydrous $MgSO_4$, is concentrated in vacuo to give 5.0 gm of crude product. This is recrystallized several times from acetone/methanol to afford 1.6 gm (yield 30%) of the product, m.p. 184°–186° C.

EXAMPLE 8

1-(4,5-Dihydro-2-thiazolyl)-1,3-dihydro-3-(2-pyridinyl-methylene)-2H-indanone

A. 3-(2-Pyridinylmethylene)-indolin-2-one

A mixture of oxindole (37.5 g, 0.28 mole), pyridine2-carboxyaldehyde (31.8 g, 0.29 mole) and pyrrolidine (21 ml) in 90 ml of methanol is heated on a steam bath. Within a short time an exothermic reaction occurs, resulting in the deposition of a thick solid mass. The solids are collected, washed with methanol and recrystallized from methanol to give 52.5 g of product: m.p. 204°–205°.

B.
1-(4,5-Dihydro-2-thiazolyl)-1,3-dihydro-3-(2-pyridinylmethylene)-2H-indanone

To a stirred suspension of NaH (1.2 g, 50 mmole) in dry tetrahydrofuran (50 ml) at room temperature under $N_2$ is added a solution of 3-(2-pyridinylmethylene)-indolin-2-one (8.9 g, 40 mmole) in dry tetrahydrofuran (200 ml). After stirring for an additional hour, the solution is cooled to 0° in an ice bath and a solution of 2-chloroethylisothiocyanate (4.9 g, 40 mmole) in dry tetrahydrofuran (50 ml) is added. The mixture is heated at reflux temperature for 3 hours.

The solution is filtered and the solids are washed several times ($CHCl_3$). The combined filtrate and washings are concentrated in vacuo to give a dark residue. The dark residue is extracted with boiling hexane several times giving, upon removal of hexane in vacuo, a residue of 4.5 g. This residue is applied to a column of Basic Alumina (Act I, 200 g) and eluted with ethyl acetate/hexane (0/100 to 100/0). The fractions eluting with 30/70 to 100/0 ethyl acetate/hexane are combined and concentrated in vacuo to give a green colored solid. Crystallization several times from methanol/$H_2O$ affords the product (1.3 g, 10.5%), m.p. 161°–163°.

EXAMPLE 9

1-(5,6-Dihydro-4H-1,3-thiazin-2-yl)-1,3-dihydro-3-(phenylmethyl)-2H-indol-2-one

The product of Example 2 [1-(5,6-dihydro-4H-1,3-thiazin-2-yl)-1,3-dihydro-3-(phenylmethylene)-2H-indol-2-one] is dissolved (partially) in 100 ml of absolute ethanol and hydrogenated over Raney-Nickel at a pressure of about 3 atmospheres (1.25 hour).

The catalyst is removed by filtration and the filtrate is concentrated in vacuo. The residue is dissolved in a small amount of ethyl acetate and applied to a column (Basic Alumina, Act. I, 25 g, dry packed) and eluted with hexane/ethyl acetate (100/0 to 80/20), then cyclohexane/ethyl acetate (100/0 to 80/20). Each fraction is concentrated in vacuo and the residue is extracted into boiling hexane. Upon cooling, crystals are formed and collected by filtration. The filtrate is combined with the subsequent column fraction and the process is repeated until more crystals are obtained. The total crystals thus obtained are combined and recrystallized from acetone/hexane to give the product (930 mg, 45%): m.p. 116°–119°.

EXAMPLES 10 to 33

Following the procedures of Example 1 or of Example 3 but substituting the indolinone derivative shown in column 1 of Table A below, the aldehyde shown in column 2 and the aliphatic haloalkylisothiocynanate shown in column 3, the product shown in column 4 is obtained.

TABLE A

| Ex. No. | R³ (position) | R¹ | Haloalkylisothiocyanate | (R³)ₙ (position) and R¹ |
|---|---|---|---|---|
| 10 | H | 3-CF₃C₆H₄ | SCN—CH₂—CH₂—CH₂—Br | As in columns 1 and 2 |
| 11 | H | C₆H₅ | SCN—CH₂—CH—Br<br>   \|<br>   CH₃ | " |
| 12 | H | C₆H₅ | SCN—CH₂—CH—Br<br>   \|<br>   C₆H₅ | " |
| 13 | Cl (6) | C₆H₅ | SCN—CH₂—CH₂—CH₂—Br | " |
| 14 | NO₂(6) | C₆H₅ | SCN—CH₂CH₂—Br | " |
| 15 | (CH₃)₂(5,6) | C₆H₅ | " | " |
| 16 | CH₃C(5)<br>   ‖<br>   O | C₆H₅ | " | " |
| 17 | CH₃(4) | C₆H₅ | " | " |
| 18 | NO₂(5) | C₆H₅ | " | " |
| 19 | CF₃(5) | C₆H₅ | " | " |
| 20 | CH₃O(6) | 3-HO—C₆H₄ | SCN—CH₂CH—Br<br>   \|<br>   C₆H₄-3-CH₃ | |
| 21 | NO₂(5) | 4-Cl—C₆H₄ | SCN—CH₂CH₂CH₂Br | |
| 22 | CN(5) | 3-NO₂—C₆H₄ | " | |
| 23 | O<br>   ‖<br>   C₆H₅C(6) | 4-CH₃C₆H₄ | " | |
| 24 | (CH₃)₂N(5) | C₆H₅ | SCN—CH₂CH—Br<br>   \|<br>   C₂H₅ | |

TABLE A-continued

| | Column 1 | Column 2 | Column 3 | Column 4 |
|---|---|---|---|---|
| | (R³)ₙ-indolin-2-one structure | R¹CHO | Haloalkylisothiocyanate | 3-(=CHR¹)-1-(thiazinyl/thiazolinyl)-indol-2-one structure |
| Ex. No. | R³ (position) | R¹ | | (R³)ₙ (position) and R¹ |
| 25 | H | 2-methylthiophen-yl | SCN—CH₂CH₂—Br | thiazoline |
| 26 | CH₃(5) | 2-methylfuran-yl | " | " |
| 27 | CF₃(6) | 5-chloro-2-methylfuran-yl | " | " |
| 28 | CH₃(7) | 3,5-dichloro-2-methylfuran-yl | " | " |
| 29 | NO₂(6) | 2-methylpyrrol-yl | " | " |
| 30 | Cl(5) | 2-methylthiazol-yl | SCN—CH₂CH₂—Br | thiazoline |
| 31 | (C₂H₅)₂N(6) | 2-methylisothiazol-yl | " | " |
| 32 | C₆H₅C(=O)(5) | 2-methylpyrimidin-yl | " | " |
| 33 | Cl(5), Cl(7) | C₆H₅ | SCN—CH₂CH₂CH₂—Br | 1,3-thiazinyl |

EXAMPLES 34 to 65

Following the procedure of Example 9 but substituting the compounds of Examples 1 and 3 to 33 as shown in column I for the 1-(5,6-dihydro-4H-1,3-thiazinyl-2-yl)-1,3-dihydro-3-(phenylmethylene)-2H-indol-2-one, the products shown in column II are obtained.

TABLE B

| | Column I | | | | Column II | | |
|---|---|---|---|---|---|---|---|
| Ex. No. | R³ (position) | R¹ | (thiazine/thiazole ring with R²) | | R³ (position) | R¹ | (thiazine/thiazole ring with R²) |
| 34 | H | C₆H₅ | 2-methylthiazoline | As in column I | As in col. I | As in col. I |
| 35 | H | C₆H₅ | 2-methyl-phenyl-thiazine | " | " | " |
| 36 | H | 4-CH₃OC₆H₄ | 2-methylthiazoline | " | " | " |
| 37 | H | 4-ClC₆H₄ | " | " | " | " |
| 38 | H | 3,4-diCl—C₆H₃ | " | " | " | " |
| 39 | H | 2-HO—C₆H₄ | " | " | " | " |
| 40 | H | (2-methylthiophene) | " | " | " | " |
| 41 | H | (2-methylpyridine) | " | " | " | " |
| 42 | H | 3-CF₃C₆H₄ | 2-methylthiazine | " | " | " |
| 43 | H | C₆H₅ | 4-methylthiazoline | " | " | " |
| 44 | H | C₆H₅ | 4-phenylthiazoline | " | " | " |
| 45 | Cl | C₆H₅ | 2-methylthiazine | " | " | " |
| 46 | NH₂(6) | C₆H₅ | 2-methylthiazoline | " | " | " |
| 47 | (CH₃)₂(5,6) | " | " | " | " | " |
| 48 | CH₃C(=O)(5) | " | " | " | " | " |
| 49 | CH₃(4) | " | " | " | " | " |
| 50 | NH₂(5) | " | " | " | " | " |
| 51 | CF₃(5) | " | " | " | " | " |
| 52 | CH₃O(6) | 3-HO—C₆H₄ | thiazoline-C₆H₄—3-CH₃ | " | " | " |

TABLE B-continued

| | Column I | | | Column II | | |
|---|---|---|---|---|---|---|
| Ex. No. | $R^3$ (position) | $R^1$ | | $R^3$ (position) | $R^1$ | |
| 53 | $NH_2(5)$ | $4\text{-}Cl\text{-}C_6H_4$ | | " | " | " |
| 54 | $CN(5)$ | $3\text{-}NO_2\text{-}C_6H_4$ | | " | " | " |
| 55 | $C_6H_5\overset{O}{\underset{\parallel}{C}}(6)$ | $4\text{-}CH_3C_6H_4$ | | " | " | " |
| 56 | $(CH_3)_2N(5)$ | $C_6H_5$ | | " | " | " |
| 57 | H | | | " | " | " |
| 58 | $CH_3(5)$ | | | " | " | " |
| 59 | $CF_3(6)$ | | | " | " | " |
| 60 | $CH_3(7)$ | | | " | " | " |
| 61 | $NH_2(6)$ | | | " | " | " |
| 62 | $Cl(5)$ | | | " | " | " |
| 63 | $(C_2H_5)_2N(6)$ | | | " | " | " |
| 64 | $C_6H_5\overset{\parallel}{\underset{O}{C}}(5)$ | | | " | " | " |
| 65 | $Cl(5)$ $Cl(7)$ | $C_6H_5$ | | " | " | " |

What is claimed is:
1. A compound of the formula

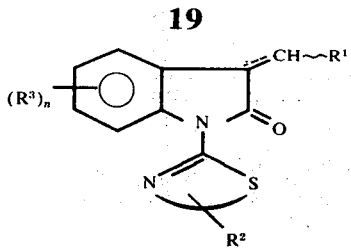

wherein R¹ is selected from the group consisting of phenyl, naphthyl, thienyl, furyl, chlorofuryl, dichlorofuryl, pyrryl, pyridyl, coumarinyl, thiacoumarinyl, thiazolyl, isothiazolyl, imidazolyl, or phenyl or naphthyl substituted with one or more substituents selected from the group consisting of halogen, hydroxy, lower alkyl, nitro, $CF_3$ and lower alkoxy; R² is selected from the group consisting of hydrogen, lower alkyl, phenyl, naphthyl, lower alkylphenyl, or lower alkylnaphthyl; R³ is selected from the group consisting of hydrogen, lower alkyl, trifluoromethyl, halo, lower alkoxy, nitro, cyano, amino, dilower alkylamino or $$\overset{O}{\underset{R-C}{\parallel}}$$

wherein R is selected from the groups consisting of lower alkyl, lower alkenyl, phenyl, phenyl-lower alkyl, cycloalkyl, cycloalkenyl, cycloalkyl-lower alkyl, and cycloalkyl-lower alkenyl;

represents a 5- or 6-membered ring selected from the group consisting of

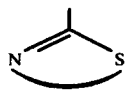

$n$ is 1 or 2; the dotted line (=) represents an optional bond; and pharmaceutically acceptable acid-addition salts thereof.

2. A compound as defined in claim 1 having the formula

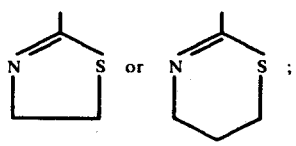

3. A compound as defined in claim 1 having the formula

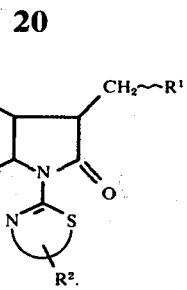

4. A compound as defined in claim 1 wherein R² is phenyl.

5. A compound as defined in claim 1 wherein R³ is hydrogen.

6. A compound as defined in claim 1 wherein R² is hydrogen.

7. A compound as defined in claim 1 wherein $n$ is 1.

8. A compound as defined in claim 1 wherein $n$ is 2.

9. A compound as defined in claim 1 wherein

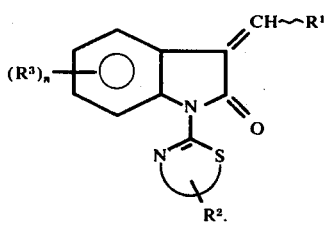

10. A compound as defined in claim 1 wherein

11. A compound as defined in claim 1 wherein R¹ is phenyl, alkoxyphenyl, halophenyl, dihalophenyl, hydroxyphenyl, (trifluoromethyl)phenyl, thienyl, or pyridyl.

12. A compound as defined in claim 1 wherein R³ is hydrogen, halo, nitro, alkyl, amino, acyl, trifluoromethyl, or dialkyl.

13. A compound as defined in claim 2 wherein R¹ is phenyl, alkoxyphenyl, halophenyl, dihalophenyl, hydroxyphenyl, trifluoromethyl phenyl, thienyl or pyridyl, and R³ is hydrogen.

14. A compound as defined in claim 3 wherein R¹ is phenyl or halophenyl and R³ is hydrogen.

15. A pharmaceutical composition comprising a compound as defined in claim 1 and a pharmaceutically acceptable carrier therefor.

16. A method for treating inflammation in mammalian species, which comprises administering to the mammalian host a therapeutic amount of a compound as defined in claim 1.

17. A compound as defined in claim 1 having the name 1-(4,5-dihydro-2-thiazolyl)-1,3-dihydro-3-(phenylmethylene)-2H-indol-2-one.

18. A compound as defined in claim 1 having the name 1-(5,6-dihydro-4H-1,3-thiazin-2-yl)-1,3-dihydro-3-(phenylmethylene)-2H-indol-2-one.

19. A compound as defined in claim 1 having the name 1-(4,5-dihydro-2-thiazolyl)-1,3-dihydro-3-[(4-methoxyphenyl)methylene]-2H-indol-2-one.

20. A compound as defined in claim 1 having the name 3-[(4-chlorophenyl)methylene]-1-(4,5-dihydro-2-thiazolyl)-1,3-dihydro-2H-indol-2-one.

21. A compound as defined in claim 1 having the name 3-[(3,4-dichlorophenyl)methylene]-1-(4,5-dihydro-2-thiazolyl)-1,3-dihydro-2H-indol-2-one.

22. A compound as defined in claim 1 having the name 1-(4,5-dihydro-2-thiazolyl)-1,3-dihydro-3-[(2-hydroxyphenyl)methylene]-2H-indol-2-one.

23. A compound as defined in claim 1 having the name 1-(4,5-dihydro-2-thiazolyl)-1,3-dihydro-3-(2-thienylmethylene)-2H-indol-2-one.

24. A compound as defined in claim 1 having the name 1-(4,5-dihydro-2-thiazolyl)-1,3-dihydro-3-(2-pyridinylmethylene)-2H-indol-2-one.

25. A compound as defined in claim 1 having the name 1-(5,6-dihydro-4H-1,3-thiazin-2-yl)-1,3-dihydro-3-(phenylmethyl)-2H-indol-2-one.

* * * * *

UNITED STATES PATENT AND TRADEMARK OFFICE
CERTIFICATE OF CORRECTION

PATENT NO. : 4,002,749
DATED : January 11, 1977
INVENTOR(S) : George C. Rovnyak

It is certified that error appears in the above-identified patent and that said Letters Patent are hereby corrected as shown below:

Column 6, line 7, "$R_3$" should read --$R^3$--.

Column 10, line 67, after "until" and before "more" insert --no--.

Example 32, Column 1, $R^3$ (position), the formula should read --$C_6H_5\overset{O}{\underset{\|}{C}}(5)$--.

Column 15 and Column 17, in Table B, Column 1, the structure in the headings should read -- 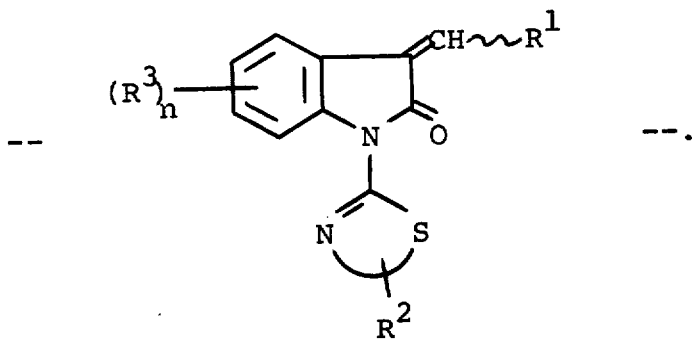 --.

Signed and Sealed this

Twenty-sixth Day of April 1977

[SEAL]

Attest:

RUTH C. MASON
Attesting Officer

C. MARSHALL DANN
Commissioner of Patents and Trademarks